United States Patent
Wassermann

Patent Number: 5,782,784
Date of Patent: Jul. 21, 1998

[54] HAND ORTHOSIS WITH INTERCHANGEABLE THUMB SUPPORT

[75] Inventor: Constance V. Wassermann, Palm Harbor, Fla.

[73] Assignee: Restorative Care of America Incorporated, Clearwater, Fla.

[21] Appl. No.: 800,119

[22] Filed: Feb. 12, 1997

[51] Int. Cl.$^6$ ............................................ A61F 5/00
[52] U.S. Cl. ....................... 602/21; 602/20; 602/62
[58] Field of Search ................. 602/5, 6, 12, 20–22, 602/64; 178/878–880; 2/20, 21

[56] References Cited

U.S. PATENT DOCUMENTS

| | | |
|---|---|---|
| 3,295,518 | 1/1967 | Hazlewood et al. |
| 3,526,006 | 9/1970 | Beardmore |
| 3,547,112 | 12/1970 | Courtney ............................ 602/21 |
| 3,703,894 | 11/1972 | Galloway et al. |
| 3,722,508 | 3/1973 | Roberts |
| 3,724,456 | 4/1973 | Waxman |
| 3,903,878 | 9/1975 | Spann ................................ 607/21 |
| 4,798,199 | 1/1989 | Hubbard et al. |
| 4,840,168 | 6/1989 | Lonardo |
| 4,862,904 | 9/1989 | West et al. |
| 4,928,712 | 5/1990 | Mele |
| 4,945,925 | 8/1990 | Garcia |
| 4,953,568 | 9/1990 | Theisler ......................... 128/879 X |
| 4,960,114 | 10/1990 | Dale ................................ 602/21 |
| 5,121,763 | 6/1992 | Bishop |
| 5,205,812 | 4/1993 | Wasserman |
| 5,437,620 | 8/1995 | Shelly ........................... 602/22 X |
| 5,447,490 | 9/1995 | Fula et al. .................... 602/21 X |
| 5,637,078 | 6/1997 | Varn |

Primary Examiner—Richard J. Apley
Assistant Examiner—Denise Pothier
Attorney, Agent, or Firm—Zarley, McKee, Thomte, Voorhees, & Sease

[57] ABSTRACT

A hand orthosis has a base member including wrist, hand, and finger portions and a cover on the base member. A cylindrical pouch is pivotally secured to the cover adjacent the hand portion and is normally movably positioned adjacent the finger portion. The pouch has an opening therein adapted to receive a detachable cylindrical pad. The cylindrical pad in the pouch has a securing element to secure the pouch in a pivotal position on the orthosis adjacent the finger portion in a position to accommodate the patient's thumb. A strap element is on the outside of the pouch to extend over the thumb of the patient wearing the orthosis to retain the thumb of the patient whose hand and fingers are supported on the hand and finger portions of the orthosis.

5 Claims, 4 Drawing Sheets

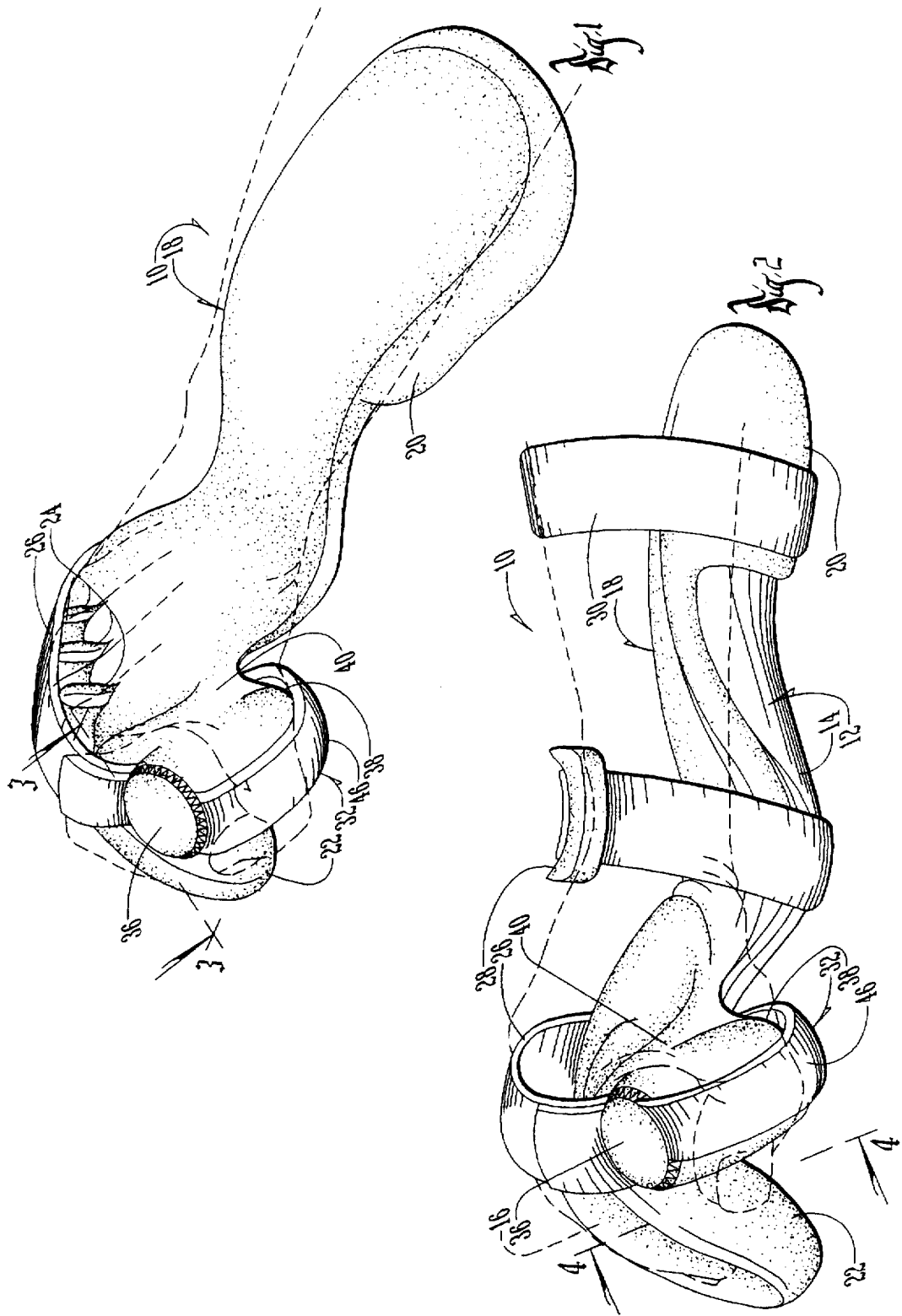

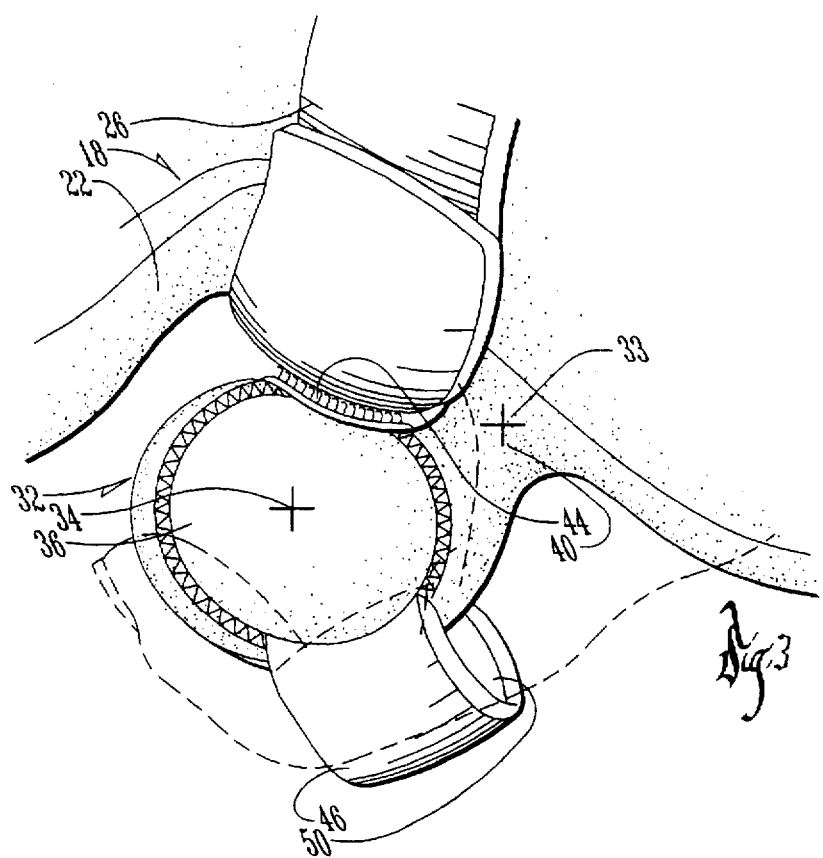
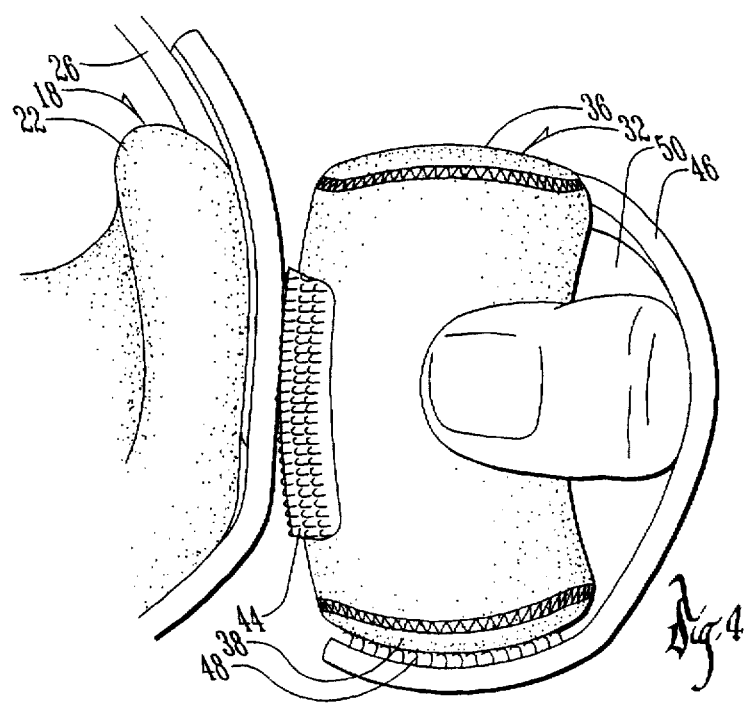

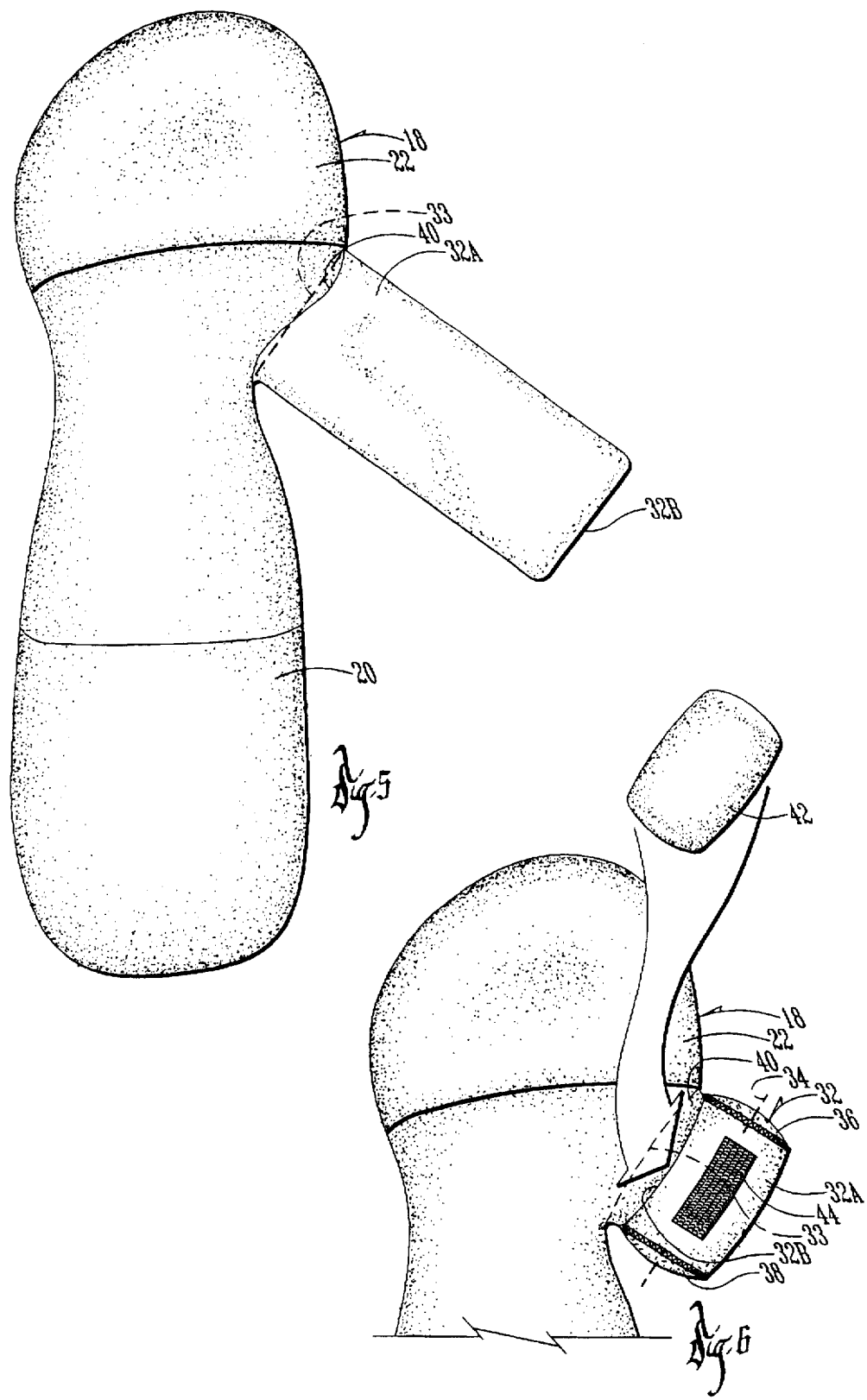

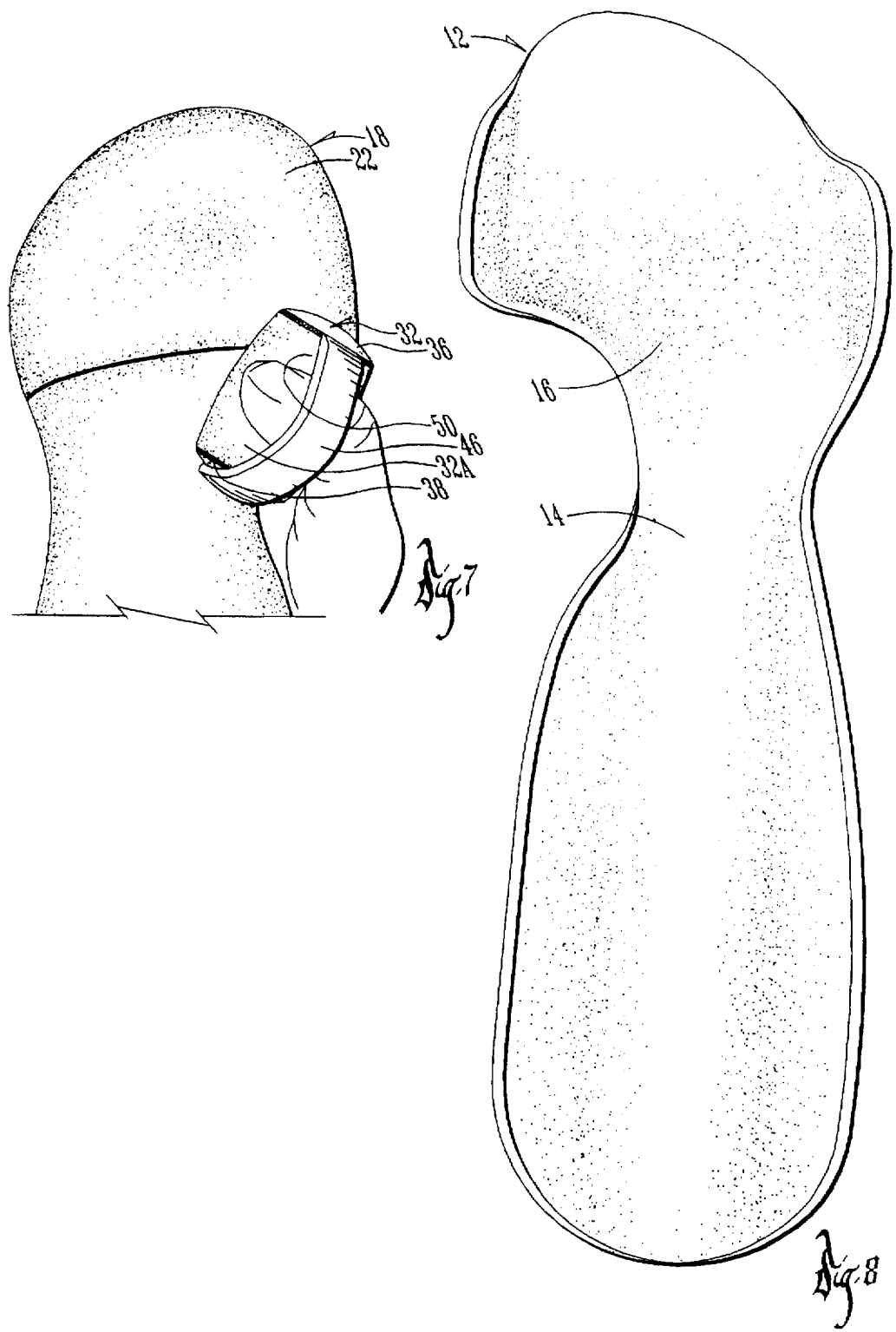

HAND ORTHOSIS WITH INTERCHANGEABLE THUMB SUPPORT

BACKGROUND OF THE INVENTION

Conventional hand orthosis provide a base member (e.g. plastic splint) which has wrist, hand, finger and thumb support surfaces with a resilient cover thereon. Straps are provided to secure the orthosis to a patient's hand.

One of the shortcomings of these devices is that there is no flexibility in varying the padded support for the thumb to adapt to different positions or configurations of a moderate to a severely adducted thumb.

It is therefore a principal object of this invention to provide a hand orthosis that will have a thumb support pad that can have a replaceable pad placed thereon to permit varying the configuration of the thumb support pad to accommodate different configurations of a patient's thumb between moderate to severe conditions of adduction.

These and other objects will be apparent to those skilled in the art.

SUMMARY OF THE INVENTION

The hand orthosis of this invention has a base member including wrist, hand, and finger portions and a cover on the base member. A cylindrical pouch is pivotally secured to the cover adjacent the hand portion and is normally movably positioned adjacent the finger portion. The pouch has an opening therein adapted to receive a detachable cylindrical pad. The cylindrical pad in the pouch has a securing element to secure the pouch in a pivotal position on the orthosis adjacent the finger portion in a position to accommodate the patient's thumb. A strap element is on the outside of the pouch to extend over the thumb of the patient wearing the orthosis to retain the thumb of the patient whose hand and fingers are supported on the hand and finger portions of the orthosis.

BRIEF DESCRIPTION OF THE DRAWINGS

FIG. 1 is a top perspective view of the device of this invention;

FIG. 2 is a side elevational view thereof as seen from the bottom of FIG. 1;

FIG. 3 is a partial end elevational view as seen on line 3—3 of FIG. 1;

FIG. 4 is a partial elevational view as seen on line 4—4 of FIG. 2;

FIG. 5 is a bottom plan view of the cover in a partially assembled condition;

FIG. 6 is a partial bottom plan view similar to FIG. 6 with the thumb pouch assembled;

FIG. 7 is a partial bottom plan view with the thumb pouch in its normal operating position; and FIG. 8 is a top plan view of the base member or splint.

DESCRIPTION OF THE PREFERRED EMBODIMENT

The orthosis 10 has a stiff but deformable plastic splint 12 which serves as a base member for the orthosis. The splint has a hand or palm portion 14, and a finger portion 16. A cover 18 of flexible material has a rearward pocket 20 into which the rearward end of splint 12 extends, and a forward pocket 22 into which the forward end of the splint extends.

Finger separators 24 extend outwardly from the top of pocket 20 (FIG. 1), and conventional straps 26, 28, and 30 are secured to the cover to attach the orthosis 10 to the hand of a patient.

A pouch 32 is cylindrical in shape and is hinged to cover 18 along large line 33 (FIG. 6). The longitudinal axis of the pouch 32 is designated by the numeral 34. The circular ends 36 and 38 are sewn into the cylindrical wall 40 to maintain the cylindrical shape of the pouch. A cylindrical resilient pad 42 is located within the pouch 32.

Pouch 32 is preferably made from a flap 32A (FIG. 5) which extends in an angular direction from the longitudinal axis of cover 18. Flap 32A is an extension of and an intregal part of the material of cover 18. The flap 32A has an outer edge 32B. FIG. 6 shows the flap 32 rolled into a hollow cylindrical shape and maintained in that shape by ends 36 and 38. When this is done, edge 32B defines a slit access opening to the resulting pouch, which can receive pad 42. The hinge line 33 is within the end portion 40 (FIGS. 3 and 5) of flap 32A opposite to edge 32B, and serves as a hinge for pouch 32 to be rotated to its operating positions in FIG. 7. The hinge line 33 is the material of cover 18 that dwells in a line adjacent pouch 32 (FIG. 6). The attachment element 44 on pouch 32 engages the inner surface of cover 18 and holds the pouch 32 in the position of FIG. 7. A thumb strap 46 has one end sewn to the end 36 with the other end detachably secured to the position by a suitable attachment element 48 to form a retaining loop 50 to secure a patient's thumb on the pouch 32 (FIG. 4).

In operation, the cover 18 is mounted on splint or base member 12 in the manner described. The pouch 32 is fitted with a pad 42 having the best size to accommodate the thumb of the patient. The orthosis 10 is placed on the hand of the patient as shown by the dotted lines in FIG. 2. The thumb strap 46 is adjusted to create a suitable loop 50 to accommodate the patient's thumb.

The attached element 44 can be detached to permit the pouch 32 to be moved from the position of FIG. 7 to that of FIG. 6 to permit different pads 42 to be inserted into the pouch through slit 32B.

The splint 12 is made of heat-moldable Kydex®. The interchangeable pads 42 provide for gentle thumb abduction for the moderate to severely adducted thumb. The cover 10 is comprised of a foam material.

It is therefore seen that this invention will at least achieve all of its stated objectives.

What is claimed is:

1. A hand orthosis having a base member including wrist, hand and finger portions, and a cover on said base member, comprising, a cylindrical pouch formed from an elongated strap having a first end and a second end, the first end secured to said cover adjacent said hand portion and the second end movably positioned adjacent said finger portions, said pouch having an opening therein adapted to receive a detachable cylindrical pad therein, a cylindrical pad in said pouch, a securing element on the outside of said pouch adapted to secure said pouch in an operating position with respect to said orthosis adjacent said finger portions, a thumb strap being on the outside of said pouch to extend over the thumb of a patient wearing said orthosis to retain the thumb of a patient whose hand and fingers are supported on said hand and finger portions.

2. The device of claim 1 wherein said pouch has opposite ends, said opening is a slit extending in a direction between said ends, and said strap being secured to one of said ends and having a free and extending longitudinally towards said other end, with a securing element on said free end to secure said strap along the length of said pouch over a patient's thumb supported thereon.

3. The device of claim 1 wherein said pad is removably mounted in said pouch.

4. The device of claim 1 wherein said pouch is hingedly secured to said cover.

5. The device of claim 1 wherein said pouch has cylindrical side walls that are an integral part of the material of said cover.

* * * * *